United States Patent [19]

Beljanski

[11] 4,335,239

[45] Jun. 15, 1982

[54] POLYRIBONUCLEOTIDES CAPABLE OF PROMOTING THE GENESIS OF LEUCOCYTES AND BLOOD PLATELETS

[76] Inventor: Mirko Beljanski, 46 Bd de Port Royal, Paris, France, 75005

[21] Appl. No.: 54,960

[22] Filed: Jul. 3, 1979

Related U.S. Application Data

[62] Division of Ser. No. 800,435, May 25, 1977, Pat. No. 4,190,649.

[30] Foreign Application Priority Data

Jun. 3, 1976 [FR] France ................................ 76 16875

[51] Int. Cl.$^3$ ............................................. C07H 21/02
[52] U.S. Cl. ........................................ 536/27; 536/28; 536/29
[58] Field of Search ................ 536/27, 28, 29; 435/91

[56] References Cited

U.S. PATENT DOCUMENTS 3,457,254 10/1966 Yano et al. ............................ 536/28

OTHER PUBLICATIONS

*The Chemistry of Nucleoside and Nucleotides*, A. M. Michelson, Academic Press, London, 1963, pp. 339–342.

*Primary Examiner*—Blondel Hazel
*Attorney, Agent, or Firm*—Bacon & Thomas

[57] ABSTRACT

The invention relates to new medicaments useful for the treatment of leucocyte and platelet deficiencies, which medicaments are polyribonucleotides prepared by degradation of the ribosomic ribonucleic acids extracted from micro-organisms or from animal organs and are formed of simple chains or "RNA fragments" comprising about 20 to 80 ribonucleotide units, the overall ratio of purine bases (G+A) to pyrimidine bases (C+U) being between 1.0 and 2.5.

The invention also relates to a process for the preparation of these polyribonucleotides by scission of the ribosomic ribonucleic acids extracted from suitable micro-organisms, by means of a ribonuclease or of a chemicl reagent such as an alkali metal base.

2 Claims, 6 Drawing Figures

POLYRIBONUCLEOTIDES CAPABLE OF PROMOTING THE GENESIS OF LEUCOCYTES AND BLOOD PLATELETS

The present application is a divisional of application Ser. No. 800,435, filed May 25, 1977, now U.S. Pat. No. 4,190,649.

This invention relates to polyribonucleotides capable of promoting generation of leucocytes and blood platelets.

Recently, in French patent application No. 74/38,768 and C. R. Acad. Sci. Paris, Series D. T. 280 (20th January 1975) pages 363–366, a process has been described for the preparation of polyribonucleotides, also called "RNA-fragments," by the action of ribonucleases which leave the guanine-adenine (G-A) sequences intact (in particular pancreatic ribonuclease) on G and A rich ribosomic ribonucleic acids extracted from bacteria or from cells of animal organs. The polyribonucleotides thus obtained comprised single-stranded chains of about 20 to 80 riboncleotide units, in which the purine bases outnumbered the pyrimidine bases, and the G-A sequence units predominated.

Figure 1:
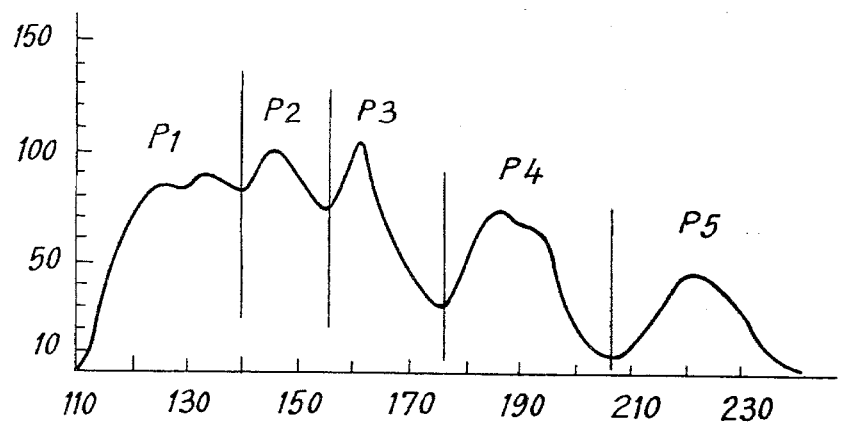

These polyribonucleotides have been selectively separated into various families by passing through a column filled with a molecular sieve marketed under the name "Sephadex G 25 fine" in a M/100 tris buffer of pH 7.4, elution being effected with the same buffer. The fractions separated in this way are called, in order of elution, $P_1$, $P_2$, $P_3$, $P_4$ and $P_5$, and correspond to the peaks of the curve shown in FIG. 1 of the accompanying drawings, in which the volume of eluate is plotted as the ordinate and the absorption measured at 260 m$\mu$ is plotted as the abscissa.

The various families of polyribonucleotides thus obtained have been analysed spectrophotometrically, and their contents of purine bases, namely guanine (G) and adenine (A), and of pyrimidine bases, namely cytosine (C) and uracil (U) determined. The families are distinguished from one another by the amount and ratio of the bases, the families $P_1$ and $P_2$ being richest in purine bases G and A.

It has already been reported that the families called $P_1$ and $P_2$, obtained from ribosomic RNA of Escherichia coli M 500, exhibit an anti-viral activity, in particular against Shope fibroma virus, cow-pox virus and herpes virus.

The present invention provides a medicament for treating leucocyte and platelet deficiencies, comprising simple chain polyribonucleotides having 20 to 80 ribonucleotide units prepared by degradation of the ribosomic ribonucleic acids extracted from micro-organisms or animal organs, the overall ratio of purine bases to pyrimidine bases $[(G+A)/(C+U)]$ in said polyribonucleotides being between 1.0 and 2.5.

It has now been found, according to the invention, that the polyribonucleotides, wherein the overall ratio of the purine bases to the pyrimidine bases $[(G+A)/(C+U)]$ is between 1.0 and 2.3, promote the genesis of leucocytes and of blood platelets and are thus useful as medicaments for encouraging leucopoiesis and the formation of platelets when a deficiency occurs.

In particular, the products called $P_3$ and $P_4$ and obtained from ribosomic RNA of *Escherichia coli* M 500 Sho-R by the action of pancreatic ribonuclease both exhibit a ratio $(G+A)/(C+U)$ of between 1.0 and 2.5, according to the invention, and are useful as "regenerator" of leucocytes and platelets.

The medicament according to the invention can be prepared in accordance with the process described in French patent application No. 74/38,768 from various sources (yeasts, bacteria and animal organs), in particular by passing E-coli M 500 Sho-R over a molecular sieve to select the fractions wherein the ratio $(G+A)/(C+U)$ is between 1.0 and 2.5.

However, the invention also relates to an improved process for the preparation of these polyribonucleotides which makes it possible to obtain them in a simpler manner and with greatly increased yield.

The invention accordingly provides a process for the preparation of the polyribonucleotides according to the invention, wherein ribosomic ribonucleic acids extracted from a micro-organism having a ratio $(G+A)/(C+U)$ from 1.0 to 2.5 are degraded by a ribonuclease or by a chemical reagent.

According to this improved process, the methods of culture of the bacteria, of isolating the ribosomic ribonucleic acids (r-RNA) and of preserving them may be identical to those described in French patent application No. 74/38,768, the improvement relating to:

(1) the choice of the bacterial strain or other starting material (fungi, yeasts or animal organs);

(2) the degradation agent used for the scission of the r-RNA into RNA fragments; and (3) the resulting elimination of the need for fractionating the product on a column.

It is preferred to use a wild non-pathogenic strain of E. coli T3000 (K 12) belonging to the species which are usually hosts of the intestinal flora. In this strain, the ratio of purine bases to pyrimidine bases is about 1.0, which is less than the ratio in the strain E. coli M 500 Sho-R. However, it is possible to use r-RNA isolated from other bacterial strains, fungi, yeasts or animal organs in which the ratio of purine bases to pyrimidine bases is satisfactory.

The agents used for the degradation can be not only ribonucleases, such as pancreatic ribonuclease or a ribonuclease extracted from Neurospora crassa, but also strong bases (sodium hydroxide or potassium hydroxide), preferably at a final concentration of 0.1 N in the reaction solution.

The RNA fragments obtained in this manner from a suitable starting material exhibit an overall ratio $(G+A)/(C+U)$ of between 1.0 and 2.5 and it is not necessary to carry out a fractionation on a column.

An example of the preparation of the fractions $P_3$ and $P_4$ from a strain of E. coli rendered resistant to showdomycin described by M. Beljanski et al. (C. R. Acad. Sci. Paris, Series D, 272, pages 2,107–2,110) and registered at the Centraal Bureau Voor Schimmelcultures, under No. CBS 615–74 and hereinafter referred to as E. coli M 500 Sho-R, is given below.

EXAMPLE 1

Preparation of $P_3$ and $P_4$ from E. coli M 500 Sho-R.

The bacteria of this strain are cultured at 37° C. in a well-aerated medium either on a rich medium containing, per liter of medium, 10 g of Bacto-tryptone, 5 g of yeast extract, 5 g of sodium chloride and sodium hydroxide solution to bring the pH to 7.3, or, if it is desired at the same time to isolate the anti-viral products $P_1$ and $P_2$ and the products $P_3$ and $P_4$, on a synthetic medium containing, per liter of medium, 100 ml of monopotassium phosphate solution containing 136 g/l, 10 ml of 20% strength ammonium sulphate solution, 1 ml of 0.05% iron sulphate solution, 1 ml of magnesium sulphate solution containing 20 g/100 ml, 2 ml of vitamin $B_1$ solution containing 0.5 part per 1,000 and potassium hydroxide solution to bring the pH to 7.2, 4 or 5 g per 1,000 of separately sterilised glucose (20% strength solution) being added to this medium after the latter has been sterilised.

At the end of the culture, the bacterial cells are collected by centrifuging and can be stored frozen. They are then homogenised in the cold in a buffer A (5 ml of 2 M tris/HCl, 30 ml of 2 M KCl, and 10 ml of a solution containing 30 g of Mg acetate/100 ml) and then ground, and their destruction is completed by ultrasonic treatment.

After dilution with a buffer B (similar to buffer A but only containing 0.1 ml of Mg acetate and 0.1 ml of mercaptoethanol), the mixture is centrifuged for 20 minutes (25 to 30,000 g) and 10 to 20 µg of desoxyribonuclease per ml are then added to the supernatant liquor. The desoxyribonuclease is allowed to act for 15 minutes at 30°-37° C. and the mixture is then centrifuged for 20 minutes (25 to 30,000 g). The supernatant liquor is then re-centrifuged for 2 hours at 40,000 rpm in an ultracentrifuge in order to collect the ribosomes and the remove the whole of the useless RNA 4 S.

The caked ribosomes are homogenised in the presence of buffer B, 2-3 drops of 20% strength lauryl-sulphate solution are added, and the mixture is subjected to thorough mechanical stirring. The ribosomic RNA is extracted by the conventional method using phenol in the presence of buffer B, several such extractions being necessary, and a final extraction with chloroform is effected in order thoroughly to remove the phenol and proteins still present.

The aqueous phases are combined and to them is added 96° strength cold alcohol containing a little KCl to assist the precipitation of the RNA. By centrifuging for 5 minutes at 5,000 g it is possible to collect the RNA which is then dialysed overnight against distilled water containing 0.1 M KCl.

In the morning, the dialysis is continued for 1 hour against distilled water only. The RNA is determined at 260 nm (U.V.) with the aid of a spectrophotometer.

The 260/280 ratio makes it possible to check whether the RNA preparation is pure. This ratio should be very close to 2.

The RNA is stored frozen or as a lyophilised powder.

The fractionation of the RNA to give polyribonucleotides (RNA fragments) is carried out as follows: 70 mg of ribosomic RNA (about 10 ml) are brought together with 0.2 ml of a solution of crystallised pancreatic ribonuclease. (The solution of pancreatic ribonuclease, containing 5 mg/ml, was beforehand boiled for 10 minutes and then cooled).

The RNA is incubated with the ribonuclease for exactly 30 minutes at 36° C. (water bath). The degradation is stopped by adding an equal volume of chloroform and stirring vigorously for a few minutes. The mixture is centrifuged for 5 minutes at 5,000 g. The aqueous phase (upper phase) is removed and, for the second time, a equal volume of chloroform is added, after which the mixture is stirred and centrifuged. The aqueous phase is immediately deposited on a column of fine Sephadex G-25 equilibrated with an $H_2O$-0.1 M tris/HCl buffer of pH 7.4.

The RNA fragments are eluted with this same buffer.

Under these conditions, 5 peaks detectable by absorption at 260 nm appear regularly, as illustrated by the elution curve. They are called from 1 to 5 in the sequence of elution from the column.

The RNA fragments which constitute peaks 1 and 2 exhibit an anti-viral activity.

The RNA fragments constituting peaks 3 and 4 always exhibit a very spectacular activity as leucocyte and platelets regenerators and constitute the medicaments according to the invention.

The RNA fragments which constitute peak 5 were not kept.

The fractions constituting each of the peaks are combined and lyophilised. The products $P_1$, $P_2$, $P_3$ and $P_4$ are thus obtained after taking up the dry residue in the minimum amount of distilled water, treating this once, vigorously, with an equal volume of chloroform, centrifuging the mixture, dialysing the supernatant liquid for 24 hours (under oxenic conditions) against sterile distilled water and lyophilising to dryness. The products $P_3$ and $P_4$ are products according to the invention, as are their mixtures in any ratios.

The constitution of the RNA fragments $P_3$ and $P_4$, which are formed of simple chains comprising from 25 to 50 nucleotides, was studied in accordance with the technique described in French Patent Application No. 74/38,768 so as to determine their contents of purine bases and pyrimidine bases.

150 µg of RNA fragments are hydrolysed for 1 hour at 100° C. (in a boiling water bath). After evaporation in a dessicator, the residue is taken up in 0.02 ml of distilled water and subjected to thin layer chromatography (ecteola cellulose) in accordance with the technique described by G. R. Björk and L. Svensson (1967, Biochim. Biophys. acta, 138, pages 430–432). The hydrolysis liberates the purine bases and the pyrimidine bases remain in the form of nucleotides.

The constituents of the RNA fragments $P_3$ and $P_4$ were separated by closed cell chromatography and identified in accordance with the technique described above for the RNA fragments $P_1$ and $P_2$.

| | | |
|---|---|---|
| The RNA fragment $P_3$ consists of: | A : 29.0 | |
| | G : 41.1 | |
| | | (G + A/C + U = 2.3) |
| | C : 15.2 | |
| | U : 15.0 | |
| The RNA fragment $P_4$ consists of: | A : 25.6 | |
| | G : 26.3 | |
| | | (G + A/C + U = 1.06) |
| | C : 21.0 | |
| | U : 27.1 | |

These figures are expressed in mols per 100 mols of nucleotides analysed, using the following extension coefficients: A=13; G=12.8; C=11.5; and U=10 and correspond to the absorption maximum (see Methods in Enzymology XII. Nucleic Acides, Part A, Ed. Grossman and K. Moldave, Academic Press (1967), page 386).

The RNA fragments $P_3$ and $P_4$ contain no trace of DNA. This was rigorously checked by colorimetry (diphenylamine) and by enzymology (activity in the presence of DNA-polymerase).

The process for the preparation of RNA fragments according to the invention from r-RNA of E. coli T 3,000, by means of various ribonucleases and by means of an alkali metal base, will now be described in Examples 2 to 4 below.

EXAMPLE 2

Degradation of r-RNA of E. coli T 3,000 by pancreatic ribonuclease A

The r-RNA were obtained from a culture of E. coil T 3,000 by a processidentical to that described in Example 1 for the r-RNA of E. coli M 500 Sho-R. The degradation of the RNA obtained is effected in accordance with the invention by means of a solution of pancreatic ribonuclease (grade A) containing 5 mg/ml, which has beforehand been heated to 100° C. for 10 minutes (on a boiling water bath) and then cooled rapidly.

A mixture of r-RNA and ribonuclease is incubated at 36° C., the ribonuclease concentration being the same as in Example 1, but the incubation time being shorter, namely 20 minutes (instead of 30 minutes). [If a different, more or less crystalline, sample of pancreatic ribonuclease is used, it is necessary to adapt the ribonuclease concentration or the incubation time].

The reaction is stopped by adding a solution of phenol containing 10% of distilled water (1 volume of this solution per 1 volume of reaction mixture), and this mixture is stirred vigorously so as to remove the ribonuclease. After centrifuging for 5 minutes at 10,000 rpm, the aqueous (upper) phase then has an equal volume of phenol added to it, and the mixture is stirred and then centrifuged. The operation is repeated with chloroform (using equal volumes). After separating the phases and repeating the operation two or three times, the aqueous phase is dialysed under axenic conditions for 16 hours against sterile distilled water at 4° C.

The amount of non-dialysable RNA fragments is determined by absorption in the ultraviolet at 260 nm. The yield of active RNA fragments, relative to the initial amount of ribosomic RNA, varies from 50 to 60%.

The RNA fragments are stored after lyophilisation.

Figure 2:
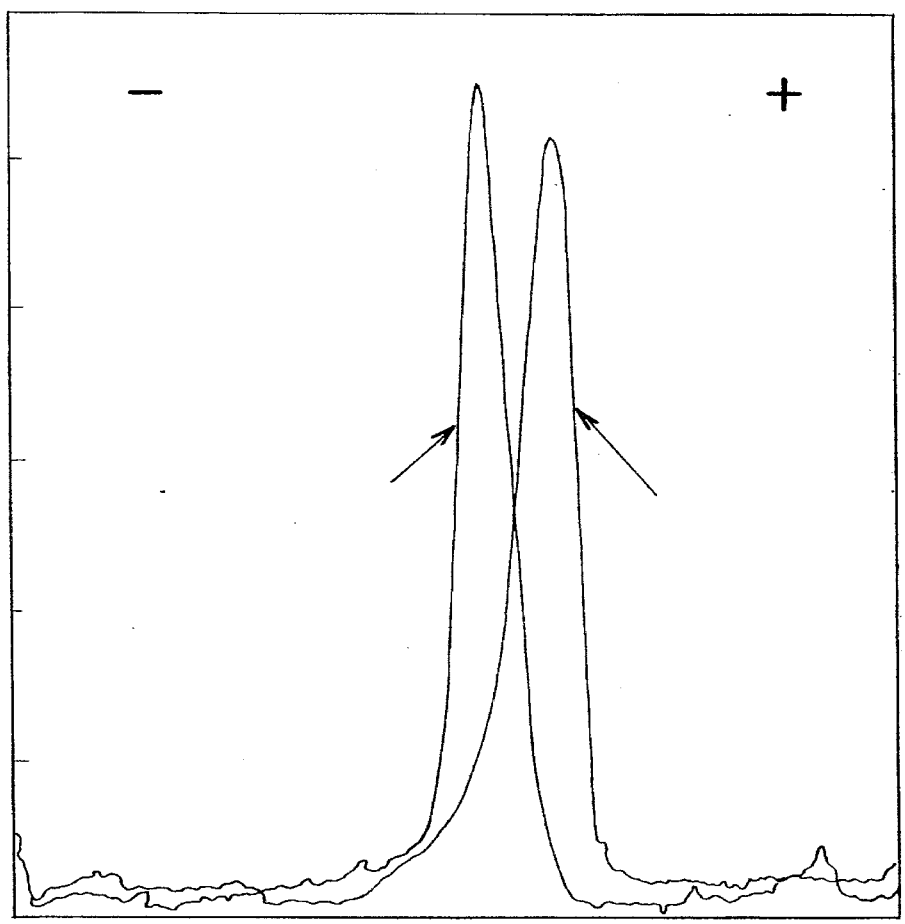

Electrophoresis, on acrylamide gel, of the RNA fragments reveals the presence of a single peak of RNA fragments of smaller size than that of the 4 S transferred RNA, as is shown by the attached FIG. 2, in which the absorption at 260 nm has been plotted as ordinates and the distance travelled in 1 hour 30 minutes as abscissae (a method described by M. Beljanski, P. Bourgarel and Mrs. M. Beljanski; Ann. Inst. Pasteur 1970, 118, page 253).

EXAMPLE 3

Degradation of the r-RNA of E. coli T 3,000 by ribonuclease $N_1$

Ribonuclease $N_1$, originating from Neurospora crassa and prepared and purified as described by K. Kasai et al., J. Bio. Chem. 1969, 66. page 389, and crystallised once, degrades the polyribonucleotide chains at the base G and its controlled action on the r-RNA makes it possible to obtain RNA fragments which are active in leucopoiesis and in the formation of blood platelets. The following conditions are used: 100 mg of r-RNA of E. coli T 3,000 dissolved in distilled water are incubated in the presence of 0.73 ml of ribonuclease $N_1$ (initial solution of 1,000 units/2 ml). Incubation time: 30 minutes at 36° C. The ribonuclease is immediately removed by the phenol and the chloroform as described in the case of ribonuclease A; the fragments are dialysed against sterile distilled water. The product obtained is lyophilised.

EXAMPLE 4

Degradation of the r-RNA of E. coli T 3,000 by sodium hydroxide solution or potassium hydroxide solution To a solution of 7 to 10 mg of r-RNA/ml is added a solution of NaOH or KOH so as to bring the final concentration of the latter to 0.1 N.

The incubation is carried out at 36° C. for 30 minutes. The mixture is immediately neutralised with an equal volume of 0.1 N HCl. The solution is dialysed against distilled water for 16 hours at 4° C. The non-dialysable product obtained is lyophilised. After hydrolysis of the various RNA fragments of Examples 2, 3 and 4, the ratio of purine bases/pyrimidine bases was determined. The results are given in the table below and expressed in mols per 100 mols of nucleotides analysed.

TABLE

| Bases | RNA fragments of Example 2 | RNA fragments of Example 3 | RNA fragments of Example 4 |
| --- | --- | --- | --- |
| G | 42.0 | 24.3 | 34.0 |
| A | 28.8 | 26.8 | 23.1 |
| C | 15.7 | 25.0 | 21.2 |
| U | 13.5 | 23.6 | 21.7 |
| ratio (G + A)/(C + U) | 2.3 | 1.06 | 1.36 |

No significant difference is observable between the RNA fragments obtained by the various degradation agents mentioned above and when using the conditions described above; the sizes of the fragments are virtually identical and always less than that of RNA 4 S (see FIG. 2).

Pharmacological properties

The distribution, in the organism, of RNA fragments $P_3$ and $P_4$ of Example 1, marked with $^{14}C$, was studied after intravenous injection into mice or rabbits.

Figure 3:
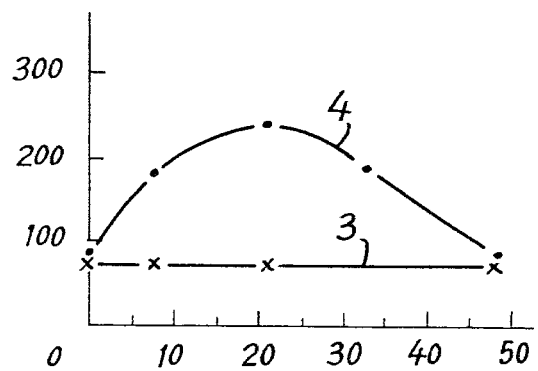
Figure 4:
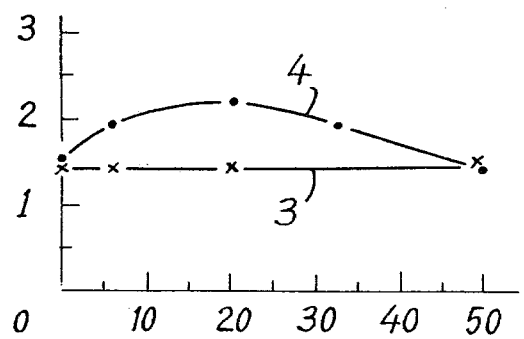

The RNA fragment $P_4$ marked with $^{14}C$ essentially settles in the spleen and to a lesser extent in the liver, and is also to be found in the bone marrow. The RNA fragment $P_3$ marked $^{14}C$ also settles and essentially in the same organs, but to a lesser degree. On killing the mice treated with these products, an increase in the volume and weight of the spleen (shown in FIGS. 3 and 4) is found solely in the case of the animals treated with $P_4$. In FIG. 3, the weight of the spleen (in mg) has been plotted as ordinates, and in FIG. 4 the weight of the liver (in g) has been plotted as ordinates, in each case as a function of the number of days (plotted as abscissae) which elapsed after the animal was given a dose of 0.3 mg of product $P_3$ (curves 3) of $P_4$ (curves 4), intravenously or intraperitoneally, per 20 g of weight of the mouse. The two organs regained their normal weight after 5 to 6 weeks and radioactivity was no longer found, having undergone natural elimination.

The action on the genesis of the leucocytes and the platelets was studied in rabbits treated with methotrexate. In animals which were given methotrexate (35 mg intramuscularly in the case of rabbits), a decrease of about 30% in the leucocytes 48 hours after administration of the antimitotic agent was found. Of 3 rabbits used for the experiment, 1 rabbit was then subcutaneously given 2 mg of the mixture of $P_3+P_4$ (in the weight ratio of 1:1); 1 rabbit was given the same dose intraperitoneally and a third rabbit was only given methotrexate (comparison). The two rabbits treated with $P_3+P_4$ regained a virtually normal number of leucocytes in 5–7 days whilst the comparison rabbit only recovered this normal number after about 15 days.

These same rabbits were subsequently given a second dose of methotrexate (55 mg intravenously, per rabbit), on day 0 in FIG. 5.

Two days afterwards, 1 rabbit was given 5 mg of $P_3+P_4$ (weight ratio 1/1.5) intraperitoneally, 1 rabbit was given the same dose subcutaneously and the third rabbit (the same comparison animal as in the preceding experiment) only received the methotrexate. The results of the analysis of the number of leucocytes in the blood sampled every two days for 20 days are illustrated by FIG. 5.

Figure 5:
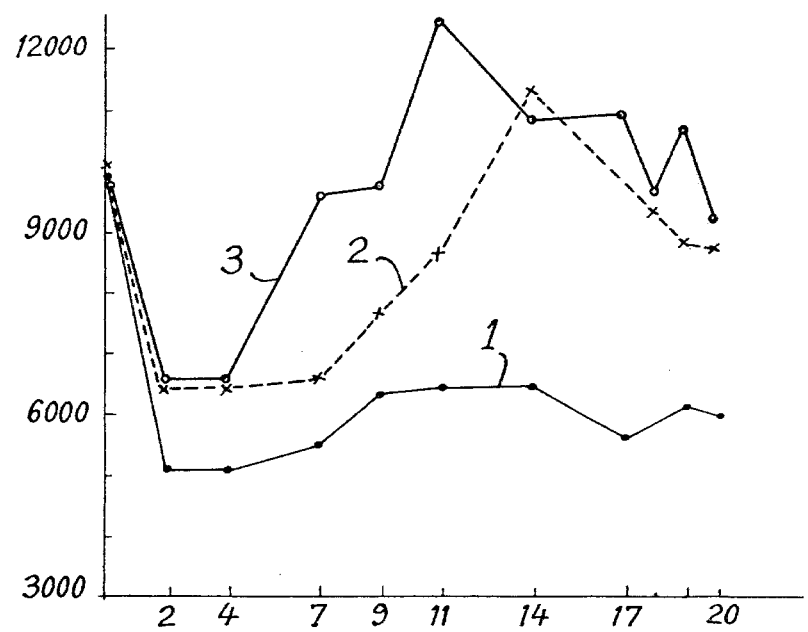

In FIG. 5, the number of leucocytes is plotted as ordinates as a function of the number of days (plotted as abscissae) which have elapsed after the injection of methotrexate; it is seen that the action of the methotrexate manifests itself, in the three rabbits, by a very great lowering of the number of leucocytes (comparison results: curve 1), but this lowering was less in the case of the two rabbits previously treated with $P_3+P_4$ subcutaneously (curve 2) or intraperitoneally, than in the case of the comparison rabbit.

In the case of the rabbit which was given $P_3+P_4$ intravenously a second time (curve 3), the leucocyte number becomes normal in 48 hours and increases for 24 or 48 hours before stabilising rapidly. In the case of the rabbit which was given $P_3+P_4$ subcutaneously, curve 2, representing the increase in the number of leucocytes, reaches its maximum about the sixth day and then stabilises (FIG. 5). In contrast, in the case of the comparison rabbit (not treated with $P_3+P_4$), the number of leucocytes remains at a low level and the animal does not succeed in regaining a normal number over the period of observation.

The number of red corpuscles in the rabbits treated in this way does not vary.

The pharmacological studies carried out with the RNA fragments obtained with various degradation agents in accordance with Examples 2 to 4 have shown that there is no significant difference in respect of the activity regarding leucopoiesis and regarding the formation of platelets, between the products $P_3$ and $P_4$ of Example 1 administered by themselves or administered as a mixture in any ratio, and each of the products of Examples 2 to 4.

Figure 6:
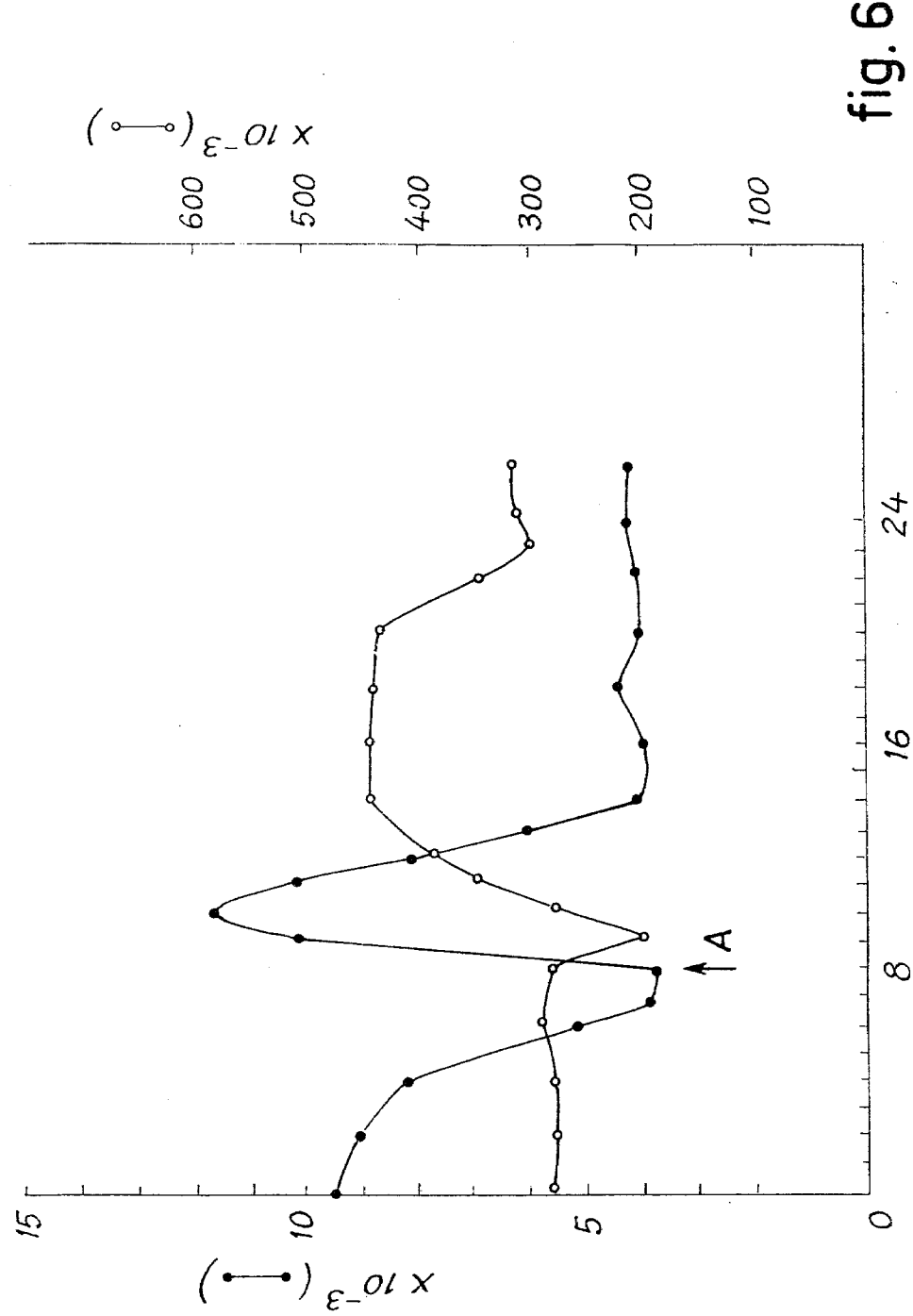

A single dose of each of the products of Examples 2 to 4 (2 to 5 mg) administered intravenously to strongly and constantly immunodepressed rabbits (leucocyte number lowered by 60 to 70%) makes it possible to re-establish a normal number of leucocytes in 24–48 hours. The number of platelets can be increased by these RNA fragements by 50 to 100% relative to the number of platelets of the comparison animals. FIG. 6 illustrates the results obtained over the duration of an experiment (20 to 30 days) with rabbits continuously treated with Endoxan (65 mg/day) and periodically treated with the RNA fragments obtained in accordance with one or other of Examples 1 to 4.

In FIG. 6, the number of days of the experiment over which the rabbits were given 65 mg of Endoxan per day has been plotted as abscissae. At the time indicated by the arrow A, the rabbits received 2 mg of RNA fragments intravenously. One of the curves of FIG. 6 was obtained by plotting the number of leucocytes as ordinates and the other curve by plotting the number of platelets as ordinates.

All routes can be used for the injection of the active RNA fragments, namely intramuscular injection (I.M.), intravenous injection (I.V.), subcutaneous injection (S.C.) and intradermal injection (I.D.); oral administration is also possible. The "response" time varies with the route chosen and depends on the dose of product. In rabbits not treated with Endoxan, which have a normal blood composition, the intravenous administration of RNA fragments does not alter the number of white corpuscles. If the dose of product is high, an increase is found, but in 24 hours the number of white corpuscles again becomes normal.

The action of various chemical and physical agents (Endoxan, Methotrexate, Thiotepa or radiation), and even a genetic deficiency causing a decrease in leucopoiesis or a decrease in platelets can, from this point of view, be counterbalanced by the action of the various abovementioned RNA fragments. The action on the genesis of platelets is less rapid than that on the white corpuscles, but does allow a large gradual recovery to take place.

The prolongation of the chemotherapy requires a repetition of the administration of the RNA fragments without causing exhaustion of the phenomenon.

Toxicology

The products $P_3$ and $P_4$ of Example 1 and those of Examples 2 to 4, dissolved in sterile physiological water, were administered to mice and rabbits intravenously, intraperitoneally, intramuscularly, subcutaneously and orally. Doses of 1 to 5 mg given as a single injection to mice and of 4 to 25 mg to rats, these injections being repeated on several days and for up to 15 days in succession did not make it possible to detect any toxic effect of the products.

Markedly higher doses, administered orally, also did not show a toxic effect.

Teratological studies have shown that the injection of the products according to the invention into female mice in gestation has no adverse effect either on the first generation or on subsequent generations.

The products according to the invention accordingly are perfectly harmless to animals.

Therapeutic application

Tests have shown that the products according to the invention can be administered each time one is dealing with leucopenia or a platelet deficiency, so as to bring the number of leucocytes and of platelets back to normal, without altering the remainder of the blood composition. A re-equilibration between the various types of white corpuscles takes place.

Since the products are soluble in water, they can be administered by any parenteral route, in the form of physiological solutions, or orally as any of the conventional galenical forms (potable solutions, tablets, pills and the like). The dose to be administered can vary from 10 to 20 mg depending on the nature of the illness to be treated, and the pharmaceutical compositions according to the invention contain, as the active product, at least one of the products according to the invention, at a unit dose of 2 to 100 mg, combined with a suitable pharmaceutical vehicle.

I claim:

1. A process for the preparation of single-stranded chain polyribonucleotides having 20 to 80 ribonucleotide units and in which the sequence units G-A predominate, the overall ratio of purine bases to pyrimidine bases (G+A)/(C+U) in said polyribonucleotides being between 1.0 and 2.5, comprising the steps of: extracting ribosomic ribonucleic acids from a microorganism having a ratio (G+A)/(C+U) from 1.0 to 2.5, degrading said ribonucleic acid extract by mixing it with a sodium or potassium hydroxide solution at a molar concentration of 0.1 N, incubating the resulting reaction mixture for 30 minutes at 36° C., immediately neutralizing said mixture with an equal volume of 0.1 N hydrochloric acid, dialysing the solution obtained against distilled water for about 16 hours, collecting the non-dialysable fraction, and lyophilising said fraction.

2. A process according to claim 1, wherein said microorganism is *Escherichia coli* T 3000.

* * * * *